United States Patent
Yamazaki et al.

(10) Patent No.: US 7,329,318 B2
(45) Date of Patent: Feb. 12, 2008

(54) METHODS OF CRYSTAL PRECIPITATION

(75) Inventors: Shigeya Yamazaki, Osaka (JP); Taichi Yoshikawa, Osaki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 268 days.

(21) Appl. No.: 10/527,317

(22) PCT Filed: Sep. 17, 2003

(86) PCT No.: PCT/JP03/11805

§ 371 (c)(1),
(2), (4) Date: Mar. 10, 2005

(87) PCT Pub. No.: WO2004/026860

PCT Pub. Date: Apr. 1, 2004

(65) Prior Publication Data

US 2006/0048696 A1    Mar. 9, 2006

(30) Foreign Application Priority Data

Sep. 19, 2002  (JP) .............................. 2002-273901

(51) Int. Cl.
C30B 7/04 (2006.01)
(52) U.S. Cl. ............................................ 117/68; 117/2
(58) Field of Classification Search ............ 117/2, 117/68

See application file for complete search history.

(56) References Cited

U.S. PATENT DOCUMENTS 4,721,723 A * 1/1988 Barnes et al. ............... 514/321
5,948,914 A * 9/1999 Sugi et al. ................... 546/240

FOREIGN PATENT DOCUMENTS

| EP | 2 234 03 A2 | 5/1987 |
| EP | 0223403 B1 | 5/1987 |
| EP | 0812827 A1 | 12/1997 |
| WO | WO-00/32593 A1 | 6/2000 |
| WO | WO-02/17921 A2 | 3/2002 |
| WO | WO-02/102382 A1 | 12/2002 |

OTHER PUBLICATIONS

Buxton et al., International Journal of Pharmaceuticals, vol. 42, p. 135-143, (1988).
Sugi et al., Chem. Pharm. Bull., vol. 48, No. 4, pp. 529-536, (2000).
Buxton, P.C. et al., International Journal of Pharmaceuticals, 1988, vol. 42, No. 1-3, p. 135-43.

* cited by examiner

*Primary Examiner*—Felisa Hiteshew
(74) *Attorney, Agent, or Firm*—Birch, Stewart, Kolasch & Birch, LLP.

(57) ABSTRACT

Crystals of paroxetine hydrochloride ½-hydrate are allowed to separate out by adding water to a solution or suspension comprising paroxetine hydrochloride and a polar organic solvent which contains no water or at most 60% by weight of water to adjust the water content to at least 70% by weight when crystals of paroxetine hydrochloride ½-hydrate are allowed to separate out in a water-containing polar organic solvent. Crystals of paroxetine hydrochloride ½-hydrate being not colored in pink can be allowed to separate out in the presence of hydrogen chloride when crystals of paroxetine hydrochloride ½-hydrate are allowed to separate out in water or a water-containing polar organic solvent.

21 Claims, No Drawings

METHODS OF CRYSTAL PRECIPITATION

This application is a 35 USC 371 application of PCT/JP2003/011805, filed Sep. 17, 2003, which claims priority of Japanese application 2002-273901, filed Sep. 19, 2002, pursuant to 35 USC 119.

TECHNICAL FIELD

Crystals of paroxetine hydrochloride ½-hydrate [(−)-(3S, 4R)-4-(4-flourophenyl)-3-[3,4-methylenedioxy)phenoxymethyl]piperidine monohydrochloride hemihydrate] have been used worldwide as an antidepressant. The present invention relates to a method for allowing such crystals of paroxetine hydrochloride ½-hydrate to separate out efficiently, and novel crystals of paroxetine hydrochloride ½-hydrate.

BACKGROUND ART

A conventional method for allowing crystals of paroxetine hydrochloride ½-hydrate to separate out with a polar organic solvent such as a lower alcohol, which contains water or no water, is a method for crystallization with 2-propanol containing 10% of water as a solvent (see, for instance, International Journal of Pharmaceutics, 42 (1988), 135-143 (p. 136, left column, the first paragraph)). Also, there is a method for crystallization by recrystallizing paroxetine hydrochloride using IMS (industrial methanol) as a solvent for recrystallization (see, for instance, Example 3(a) in EP 223403 B1 corresponding to JP-B-6-47587; and Example 4(a) of UK Patent Application No. 8526407). Also, there are some examples in which only water is used as a solvent for crystallization without using a polar organic solvent (see, for instance, Examples 2 and 3(b) in EP 223403 B1; and Examples 3 and 4(b) in UK Patent Application No. 8526407).

In addition, an attempt to solve a problem of coloration in pink with paroxetine hydrochloride was made in WO 02/102382, which was laid open to public inspection after the priority date of the present application. In this method, when paroxetine hydrochloride is prepared by a reaction of a paroxetine base with HCl, HCl is used in an amount of less than 1 mole equivalent or in such an amount that the pH becomes about 3 to about 8, due to a disadvantage that, for instance, impurities are produced when HCl (pH: at most 1) is used in a small excess amount. As Far as the present inventors know, toluene which is a non-polar solvent has been used as a solvent for the preparation of paroxetine hydrochloride in the existence of a small excess amount of HCl (see EP 223403 B1 and UK Patent Application No. 8526407).

DISCLOSURE OF INVENTION

The inventors have intensively studied various methods for allowing crystals of paroxetine hydrochloride ½-hydrate to separate out with a polar organic solvent to provide a method for crystallization, not causing the above problems. As a result, the present inventors have found that crystals of paroxetine hydrochloride ½-hydrate separate out in a high yield when water is added to a solution or suspension of paroxetine hydrochloride, the solvent of which is a polar organic solvent containing no water or at most 60% by weight of water, to adjust the water content to at least 70% by weight, and have completed the present invention. The present inventors found that the solubility of paroxetine hydrochloride ½-hydrate becomes particularly higher in a polar organic solvent containing 10 to 60% by weight of water than that in a polar organic solvent containing no water, with the exception of examples such as methanol, and that crystals efficiently separate out when water is added to the solution or suspension, to adjust the water content to at least 70% by weight, and the present invention has been thus completed.

In addition, the present inventors found that a problem such as coloration of crystals of paroxetine hydrochloride ½-hydrate obtained by a method for crystallization in an aqueous solvent or a polar organic solvent containing water in pink can be solved by allowing crystals to separate out in the presence of hydrogen chloride, and completed the present invention.

Specifically, one of the present inventions is:

(1) a method for allowing crystals of paroxetine hydrochloride ½-hydrate to separate out, characterized in that water is added to a solution or suspension comprising paroxetine hydrochloride and a polar organic solvent which contains no water or at most 60% by weight of water, to adjust the water content to at least 70% by weight, when crystals of paroxetine hydrochloride ½-hydrate are allowed to separate out in a water-containing polar organic solvent;

(2) the method for allowing crystals of paroxetine hydrochloride ½-hydrate to separate out according to the item (1) mentioned above, wherein the solution or suspension of a solid or oily paroxetine hydrochloride is prepared, and water is added to the solution or suspension to adjust the water content to at least 70% by weight;

(3) the method for allowing crystals of paroxetine hydrochloride ½-hydrate to separate out according to the item (1) mentioned above, wherein the solution or suspension of crystals of paroxetine hydrochloride is prepared, and water is added to the solution or suspension to adjust the water content to at least 70% by weight;

(4) the method for allowing crystals of paroxetine hydrochloride ½-hydrate to separate out according to the item (1) mentioned above, wherein the solution or suspension of crystals of paroxetine hydrochloride anhydrate is prepared, and water is added to the solution or suspension to adjust the water content to at least 70% by weight;

(5) the method for allowing crystals of paroxetine hydrochloride ½-hydrate to separate out according to the item (1) mentioned above, wherein the solution or suspension of crystals of 2-propanol solvate of paroxetine hydrochloride anhydrate obtained by crystallization in 2-propanol is prepared, and water is added to the solution or suspension to adjust the water content to at least 70% by weight;

(6) the method for allowing crystals of paroxetine hydrochloride ½-hydrate to separate out according to the item (1) mentioned above, wherein the solution or suspension of crystals of paroxetine hydrochloride ½-hydrate is prepared, and water is added to the solution or suspension to adjust the water content to at least 70% by weight;

(7) the method for allowing crystals of paroxetine hydrochloride ½-hydrate to separate out according to any one of the items (1) to (6) mentioned above, wherein water is added to the solution or suspension comprising paroxetine hydrochloride and a polar organic solvent containing 15 to 55% by weight of water;

(8) the method for allowing crystals of paroxetine hydrochloride ½-hydrate to separate out according to any one of the items (1) to (6) mentioned above, wherein water is added to the solution or suspension comprising paroxetine hydrochloride and a polar organic solvent containing 20 to 50% by weight of water;

(9) the method for allowing crystals of paroxetine hydrochloride ½-hydrate to separate out according to any one of the items (1) to (8) mentioned above, wherein water is added to the solution or suspension comprising paroxetine hydrochloride at 40° to 60° C.;

(10) the method for allowing crystals of paroxetine hydrochloride ½-hydrate to separate out according to any one of the items (1) to (9) mentioned above, wherein water is added to the solution or suspension of paroxetine hydrochloride, and then the resulting solution or suspension is cooled to 0° to 10° C.;

(11) the method for allowing crystals of paroxetine hydrochloride ½-hydrate to separate out according to any one of the items (1) to (10) mentioned above, wherein the polar organic solvent is a lower alcohol or a ketone;

(12) the method for allowing crystals of paroxetine hydrochloride ½-hydrate to separate out according to any one of the items (1) to (11) mentioned above, wherein the lower alcohol is 2-propanol; and

(13) the method for allowing crystals of paroxetine hydrochloride ½-hydrate to separate out according to any one of the items (1) to (12) mentioned above, wherein hydrogen chloride is present in the solution or suspension of paroxetine hydrochloride.

Also, another of the present invention is:

(14) a method for allowing crystals of paroxetine hydrochloride ½-hydrate to separate out, characterized in that hydrogen chloride is present when crystals of paroxetine hydrochloride ½-hydrate are allowed to separate out from the solution or suspension of paroxetine hydrochloride in which water or a water-containing polar organic solvent is used as a solvent, with the exception of the case where concentrated hydrochloric acid is added to an aqueous solution of paroxetine acetate;

(15) the method for allowing crystals of paroxetine hydrochloride ½-hydrate to separate out according to the item (14) mentioned above, wherein the pH of the solution or suspension of paroxetine hydrochloride is at most 2;

(16) the method for allowing crystals of paroxetine hydrochloride ½-hydrate to separate out according to the item (14) or (15) mentioned above, wherein the solution or suspension of a solid or oily paroxetine hydrochloride is prepared, and water is added to the solution or suspension to adjust the water content to at least 70% by weight;

(17) the method for allowing crystals of paroxetine hydrochloride ½-hydrate to separate out according to the item (14) or (15) mentioned above, wherein the solution or suspension of crystals of paroxetine hydrochloride is prepared, and water is added to the solution or suspension to adjust the water content to at least 70% by weight;

(18) the method for allowing crystals of paroxetine hydrochloride ½-hydrate to separate out according to the item (14) or (15) mentioned above, wherein the solution or suspension of crystals of paroxetine hydrochloride anhydrate is prepared, and water is added to the solution or suspension to adjust the water content to at least 70% by weight;

(19) the method for allowing crystals of paroxetine hydrochloride ½-hydrate to separate out according to the item (18) mentioned above, wherein the crystals of paroxetine hydrochloride anhydrate are crystals of 2-propanol solvate of paroxetine hydrochloride anhydrate obtained by crystallization in 2-propanol;

(20) the method for allowing crystals of paroxetine hydrochloride ½-hydrate to separate out according to the item (14) or (15) mentioned above, wherein the solution or suspension of crystals of paroxetine hydrochloride ½-hydrate is prepared, and water is added to the solution or suspension to adjust the water content to at least 70% by weight;

(21) crystals of paroxetine hydrochloride ½-hydrate, moisturized with water or a polar organic solvent containing water, characterized in that the crystals are not colored in pink;

(22) crystals of paroxetine hydrochloride ½-hydrate, characterized in that the pH of the supernatant of the suspension prepared by suspending 1 g of the crystals in 10 g of distilled water is 3 to 6; and

(23) a process for preparing crystals of paroxetine hydrochloride ½-hydrate being not colored in pink, comprising dissolving crystals of paroxetine hydrochloride ½-hydrate being colored in pink in a solvent for allowing crystals to separate out, characterized in that the crystals are purified in the presence of hydrogen chloride in an amount at least equimolar with the paroxetine hydrochloride ½-hydrate.

BEST MODE FOR CARRYING OUT THE INVENTION

One of the methods for crystallization of the present invention is a method as described in any one of the items (1) to (13) above (Invention 1). The embodiment of this method is described below.

According to this method, a solution or suspension of paroxetine hydrochloride and a polar organic solvent which contains no water or at most 60% by weight of water is first prepared.

The paroxetine hydrochloride may be in a solid state such as a crystalline state or an amorphous state, or an oily state which means that the paroxetine hydrochloride has not yet been solidified. Also, the solution or suspension of paroxetine hydrochloride can be used. The paroxetine hydrochloride is particularly preferably in a crystalline state, because crystals of paroxetine hydrochloride ½-hydrate having a higher purity can be obtained from this crystalline paroxetine hydrochloride when the method of the present invention is carried out.

The crystals can be any of crystals of paroxetine hydrochloride ½-hydrate and crystals of paroxetine hydrochloride anhydrate. In the case of crystals of paroxetine hydrochloride ½-hydrate, the method for crystallization of the present invention is carried out mainly for the purpose of purification of crystals. The paroxetine hydrochloride anhydrate can be any of Form 2 described in International Journal of Pharmaceutics, 42 (1988), 135-143, and various non-solvate or solvate crystals as described in WO 96/24595, JP-B-6-47587, EP 223403 B1, EP 0812827 A1 and like. Practically preferable are crystals of 2-propanol solvate of paroxetine hydrochloride anhydrate containing 2-propanol, which are crystallized from 2-propanol (the content of 2-propanol is exemplified by 14% by weight or 3% by weight or so). These crystals may be wet crystals obtained by separating the crystals from a suspension of crystals by means of filtration or the like, that is, crystals from which a solvent for crystallization has not yet been sufficiently removed by drying. There can be cited, for instance, crystals of 2-propanol solvate of paroxetine hydrochloride anhydrate containing 2-propanol, prepared by crystallizing from 2-propanol, which is moisturized with 2-propanol as a solvent for crystallization, as disclosed in item 1) of Example 9.

The solution or suspension of paroxetine hydrochloride is exemplified by the followings, but is not limited to the exemplified ones. One example is a solution or suspension of paroxetine hydrochloride, obtained by subjecting a precursor of paroxetine hydrochloride, for example, N-tert-butyloxycarbonyl-paroxetine to treating with hydrogen chloride, to deprotect the N-tert-butyloxycarbonyl group. This is a case where the method for crystallization of the present invention is carried out by using the reaction solution as it is without the isolation of paroxetine hydrochloride when the reaction solution is one containing paroxetine hydrochloride obtained by the above reaction at the post-treatment stage, and its solvent is one of the polar organic solvents as described above such as 2-propanol. Another example is a case where paroxetine hydrochloride is obtained by the salt-exchange of an acid salt of paroxetine, the acid of which is other than hydrochloric acid, such as acetate, with hydrogen chloride. When the solvent for the salt-exchange reaction used in this case is, for instance, one of the polar organic solvents used in the present invention as described in Example 2, the method for crystallization of the present invention can be carried out by using the solution or suspension of paroxetine hydrochloride obtained by the above salt-exchange reaction as it is without the isolation of paroxetine hydrochloride in some cases.

In the case where the solution or suspension of paroxetine hydrochloride is obtained by converting the precursor, acid salt or the like into paroxetine hydrochloride as described above, when the solvent is not one of the polar organic solvents used in the present invention, the solvent is exchanged for a solvent used in the present invention without the isolation of paroxetine hydrochloride, and then the solution or suspension is used for the method of the present invention.

The polar organic solvent as referred to herein is an organic solvent which is miscible with water and has a relative dielectric constant of preferably 5 to 50, more preferably 15 to 40 at 25° C. [see, "New edition, Solvent Pocket Book," pp. 1-2, edited by Synthetic Organic Chemistry Association, published by Ohmsha, Jun. 10, 1994]. Representative examples of the polar organic solvent include lower alcohols having 1 to 5 carbon atoms, such as methanol, ethanol and 2-propanol, ketones including symmetric or asymmetric, lower dialkylketones having 2 to 5 carbon atoms, such as acetone and methyl ethyl ketone, tetrahydrofuran, and the like. From the viewpoint of the solubility of paroxetine hydrochloride, the safety in terms of a residual solvent contained in pharmaceuticals, and the like, 2-propanol, ethanol and acetone are especially preferred. From the viewpoint of practical value, 2-propanol is especially preferred. The polar organic solvent may be a mixed solvent of two or more kinds of the polar organic solvents mentioned above.

The polar organic solvent may contain water. In this case, the water content is at most 60% by weight from the viewpoint of the solubility of paroxetine hydrochloride. Although the preferred range of the content varies with the kind of the solvent, the water content is preferably 10 to 60% by weight, more preferably 15 to 55% by weight, still more preferably about 20 to 50% by weight, with the exception of methanol. When the water content is within this range, the solubility of paroxetine hydrochloride is high. It is preferable to increase the solubility of paroxetine hydrochloride by controlling the water content in order to allow crystals of paroxetine hydrochloride ½-hydrate having a high purity to separate out even in the case of the suspension.

The solution or suspension of paroxetine hydrochloride is prepared by using as a solvent a polar organic solvent which does not contain water or contains water, as described above. The process for preparing the solution or suspension may be any process, as long as the process eventually provides the above solution or suspension. In the case where the solution or suspension is prepared by using isolated paroxetine hydrochloride, the paroxetine hydrochloride is usually mixed with a solvent.

In another case, the solution or suspension of paroxetine hydrochloride is obtained by converting the precursor, acid salt or the like into paroxetine hydrochloride, as described above. In this case, water may be added to adjust the water content as occasion demands.

In the present invention, either of the solution or the suspension may be used, as long as it contains paroxetine hydrochloride, and the solution is preferable from the viewpoint of the preparation of purified crystals.

When the solution or suspension of paroxetine hydrochloride is prepared, it is preferable that the solution or suspension is usually warmed or heated so that paroxetine hydrochloride is dissolved as much as possible, in order to increase the solubility of paroxetine hydrochloride, because the possibility of obtaining crystals having a higher purity is increased. However, when the temperature is excessively increased, the crystals are likely to be decomposed, so that the temperature is usually adjusted to a temperature of 40° to 60° C. To merely obtain crystals of paroxetine hydrochloride ½-hydrate without intending to increase the purity, the temperature may be a temperature equal to or higher than the temperature mentioned above or a temperature equal to or lower than the temperature mentioned above, or may be room temperature.

The amount of the polar organic solvent which contains water or no water is not limited to specified ones, as long as the solution or suspension can be prepared. The amount of the polar organic solvent is usually 1 to 10 parts by weight, preferably 2 to 5 parts by weight, based on 1 part by weight of paroxetine hydrochloride, from the viewpoint of giving a solution or suspension which is easily handled. When the solution is prepared, the solution may be purified by treating with activated carbon.

In the present invention, water is added to the solution or suspension of paroxetine hydrochloride prepared as mentioned above, to adjust the water content in the polar organic solvent containing water to at least 70% by weight, preferably 75 to 95% by weight, more preferably 80 to 90% by weight, to allow crystals to separate out.

The method for adding water is not limited to specified ones, as long as water added is diffused sufficiently throughout the solution or suspension of paroxetine hydrochloride and a large amount of crystals do not separate out at a time. When a large amount of crystals separate out at a time, the crystals tend to be too fine, so that the crystals are difficult to be separated or got out, and the crystals tend to be contaminated with impurities. Usually, water is added dropwise to the solution or suspension with stirring.

The addition rate, temperature and the like are controlled to prevent the crystallization in a large amount during the addition of water. The temperature of water added is preferably a temperature equal to or slightly lower than the temperature at which the solution or suspension is prepared, and usually 40° to 60° C. When water is added to a solution comprising paroxetine hydrochloride and 2-propanol containing at most 60% by weight of water or no water to adjust the water content to 80 to 90% by weight, substantially little crystallization is usually observed even at the stage where the water has been completely added.

After the addition of water, the resulting solution or suspension is cooled, to allow crystals to separate out. As a specific method for crystallization, conventional means being widely used for usual crystallization are employed. Specifically, the cooling rate is controlled so that a large amount of crystals do not separate out. Preferably, once crystals begin to separate out, this temperature is maintained for a certain period of time, to allow crystal growth and suppress the crystallization of too small crystals. The time period is several tens of minutes to one hour, which differs depending on the scale of production, and may be longer in a large-scale production in some cases. Crystals can be allowed to separate out by adding a seed crystal to promote the crystallization.

Thereafter, in order to allow crystals to separate out sufficiently, the solution or suspension is further cooled, and its temperature is adjusted to a temperature of 0° to 10° C., preferably 0° to 5° C. In accordance with conventional means, the solution or suspension is usually maintained at this temperature for a certain period of time, to complete the crystallization. The time period is several tens of minutes to one hour, which differs depending on the scale of production, and may be longer in a large-scale production in some cases.

Cooling after the addition of water and maintaining the temperature as described above are usually carried out under stirring, from the viewpoint of achieving uniform temperature throughout the solution and the viewpoint of crystallization without maldistribution in a container.

Thereafter, the crystals of paroxetine hydrochloride ½-hydrate being allowed to separate out by the method of the present invention are separated by a conventional method such as filtration, washed and dried. It is preferable that hydrogen chloride is present in the solution or suspension of paroxetine hydrochloride in the above-mentioned methods of (1) to (13) for crystallization of the present invention as described below, from the viewpoint of the prevention of the resulting crystals from coloration in pink.

Another method for crystallization of the present invention (Invention 2) is a method described in any one of the items (15) to (21) for allowing crystals of paroxetine hydrochloride ½-hydrate to separate out, characterized in that hydrogen chloride is present when crystals of paroxetine hydrochloride ½-hydrate are allowed to separate out from the solution or suspension of paroxetine hydrochloride in which water or a water-containing polar organic solvent is used as a solvent, with the exception of the case where concentrated hydrochloric acid is added to a solution of paroxetine acetate.

According to this method, a problem arisen in the method for allowing crystals of paroxetine hydrochloride ½-hydrate to separate out from the solution or suspension of paroxetine hydrochloride in which water or a water-containing polar organic solvent is used as a solvent, such as coloration of the crystals in pink can be solved. For instance, according to the above-mentioned methods of (1) to (13) for crystallization, crystals being not colored in pink are obtained when hydrogen chloride is present in the solution or suspension of paroxetine hydrochloride.

The term "hydrogen chloride is present," as referred to herein, means that hydrogen chloride other than the hydrogen chloride constituting paroxetine hydrochloride is present.

Also, in Invention 2, when hydrogen chloride other than the hydrogen chloride constituting the paroxetine hydrochloride is present in an amount at least equimolar with the paroxetine hydrochloride, decolorized and purified crystals are obtained from the crystals being colored in pink. The crystals being colored in pink are obtained, for instance, by treating the crystals of paroxetine hydrochloride ½-hydrate with water at such a high temperature as 100° C.

The solution or suspension of paroxetine hydrochloride used in Invention 2, the solvent of which is water or water-containing polar organic solvent may be any solution or suspension, and include, for instance, one prepared by using 2-propanol containing 10% by weight of water as a solvent for crystallization as described in International Journal of Pharmaceutics, 42 (1988), 135-143, in particular, on p. 136, left column, the first paragraph; and those prepared by using IMS (industrial methyl alcohol) or water as a solvent for recrystallization as described in JP-B-6-47587, Example 2 of EP 223403 and the like. Also, the solution and suspension may include the solutions or suspensions comprising paroxetine hydrochloride usable in Invention 1. Incidentally, JP-B-6-47587 and Example 2 of EP 223403 disclose that crystals of paroxetine hydrochloride ½-hydrate are allowed to separate out by adding concentrated hydrochloric acid to an aqueous solution of paroxetine acetate, but there is no description concerning the prevention of the crystals from coloration in pink in the these publications. Moreover, these documents do not at all disclose that solid or oily paroxetine hydrochloride being isolated is dissolved in water or a water-containing polar organic solvent, and that hydrogen chloride is presented in the solution. Incidentally, concentrated hydrochloric acid refers to a concentrated hydrochloric acid having a meaning being usually employed, and is an aqueous solution prepared by dissolving hydrogen chloride (HCl) gas in water to an approximately saturated solution. More specifically, the concentrated hydrochloric acid as used herein means an aqueous solution of hydrogen chloride having a hydrogen chloride concentration of at least 35%, as specified in JIS (Japanese Industrial Standard).

The paroxetine hydrochloride and the organic polar solvent include those described for Invention 1. The water content in the water-containing polar organic solvent may be any content, as long as crystals of paroxetine hydrochloride ½-hydrate are allowed to separate out. The water content is at least 5% by weight, in consideration of the amount which would cause a problem of coloration in pink. The paroxetine hydrochloride includes those described for Invention 1.

As the preparation of the solution or suspension of paroxetine hydrochloride, there can be cited those explained in Invention 1, except that the water content is not limited to at most 60% by weight.

In Invention 2, sources for hydrogen chloride other than the hydrogen chloride constituting the paroxetine hydrochloride are exemplified by hydrochloric acid which is an aqueous solution of hydrogen chloride; a solution prepared by dissolving hydrogen chloride in the polar organic solvent according to the present invention; and hydrogen chloride gas itself.

The method for supplying hydrogen chloride may be any method, as long as the method allows hydrogen chloride to be present in the step of crystallization in Invention 2, and does not interfere with the crystallization in Invention 2. A solution of hydrogen chloride or hydrogen chloride gas is usually supplied to the solution or suspension of paroxetine hydrochloride, or water or a water-containing polar organic solvent prior to the preparation of the solution or suspension.

The amount of the hydrogen chloride other than the hydrogen chloride constituting the paroxetine hydrochloride may be at least 0.05 times, preferably at least 0.1 times the amount (mole) of paroxetine hydrochloride. When crystals of paroxetine hydrochloride ½-hydrate being colored in pink are purified to give colorless crystals, the hydrogen chloride is required in an amount at least equimolar with the paroxetine hydrochloride. The amount of the hydrogen chloride can be up to 2 times the amount (mole) of paroxetine hydrochloride from the viewpoint of suppressing the coloration in pink. The hydrochloric acid can be added in an amount greater than the amount mentioned above. However, if the amount is so much, for instance, the amount is ten times the amount of paroxetine hydrochloride, and then dissolution of the paroxetine hydrochloride would be insufficient. Even so, such a large amount of hydrochloric acid can be employed with no problem for obtaining crystals of paroxetine hydrochloride ½-hydrate with suppressed coloration in pink.

When hydrogen chloride is used in the amount mentioned above, the pH of the solution or suspension comprising paroxetine hydrochloride will be at most 2. Also, when hydrogen chloride is used in an amount of at least 0.1 times the amount (mole) of paroxetine hydrochloride, the pH will be at most 1.5. According to the Examples mentioned later, the pH is determined for the filtrate obtained after filtering crystals, and this pH is considered to demonstrate the pH of the solution or suspension when the crystals are allowed to separate out.

The method for crystallization of paroxetine hydrochloride ½-hydrate from the solution or suspension of paroxetine hydrochloride in which hydrogen chloride exists can be any method, as long as paroxetine hydrochloride ½-hydrate is allowed to separate out. In case of a warmed solution or suspension, a conventional method for cooling as it is, or a method for adding water to cool as in Invention 1 can be cited. When warming is not employed, a method for adding water can be used. After crystals are allowed to separate out, usually, the solution or suspension is further cooled to at most 10° C., practically 0° to 5° C., to complete the crystallization. Thereafter, the crystals being allowed to separate out are subjected to filtration, washing and the like, and then isolated. The crystals moisturized with the solvent for crystallization just after this isolation are colored not in pink but in white according to Invention 2. According to a method for crystallization in which hydrogen chloride is absent, crystals being moisturized with the solvent tend to be colored in pink.

Then the crystals are further dried to obtain white crystals of paroxetine hydrochloride ½-hydrate being not colored in pink.

The crystals of paroxetine hydrochloride ½-hydrate obtained in Invention 2 were suspended in the amount of 1 g in 10 g of distilled water, and the pH of the supernatant of the suspension was measured. As a result, the pH was 3 to 6, usually 3 to 5.5, commonly 4.5 to 5.5, which is lower than the supernatant of the suspension of crystals obtained in the absence of hydrogen chloride.

Next, the present invention is further explained on the basis of the following examples, but the scope of the present invention is not limited only to these examples.

EXAMPLE 1

To a mixed solution of 30.0 g of 2-propanol and 30.0 g of water was added 10.0 g (27.34 mmol) of a 2-propanol solvate of a paroxetine hydrochloride anhydrate (containing about 3% by weight of 2-propanol) under nitrogen gas stream to dissolve the solvate at room temperature. Another 50 mL of water was added thereto. In the course of cooling the mixture to 5° C., crystals separated out at 20° C. After being stirred at 4° to 5° C. under ice cooling for 1 hour, the mixture was filtered at the same temperature. The residue was washed with a solution composed of 2.0 g of 2-propanol and 8.0 g of water, to give crystals colored in pink. The crystals were dried under reduced pressure at 60° C., to give 8.35 g of crystals of a paroxetine hydrochloride ½ hydrate (yield: 81.5% by weight). Its water content was 2.51% by weight (theoretical water content: 2.40% by weight). The X-ray powder diffraction pattern (XRD) agreed with that of a reference material. The pH of the filtrate was 5.75.

EXAMPLE 2

To a mixed solution of 30.0 g of 2-propanol and 28.0 g of water was added 10.64 g (27.34 mmol) of paroxetine acetate under nitrogen gas stream to dissolve the acetate at room temperature. Next, 3.13 g (equivalent to 30.05 mmol of hydrogen chloride) of 35% by weight hydrochloric acid and 50 mL of water were sequentially added to the solution. In the course of cooling the mixture to 5° C., crystals separated out at 20° C. After being stirred at 4 °to 5° C. under ice cooling for 1 hour, the mixture was filtered at the same temperature. The residue was washed with a solution of 2.0 g of 2-propanol and 8.0 g of water to give wet crystals (white). The crystals were dried under reduced pressure at a bath temperature of at most 40° C., to give 9.40 g of crystals (white) of a paroxetine hydrochloride ½ hydrate (yield: 91.8% by weight). The XRD agreed with that of a reference material. The pH of the filtrate was 1.39. The water content was 2.48% by weight (theoretical water content: 2.40% by weight).

EXAMPLE 3

To a mixed solution of 15.00 g of 2-propanol and 0.14 g of 35% hydrochloric acid (equivalent to 1.37 mmol of hydrogen chloride) was added 5.00 g (13.67 mmol) of a 2-propanol solvate of paroxetine hydrochloride anhydrate (containing about 3% by weight of 2-propanol) under nitrogen gas stream, and the mixture was heated to 50° C. Next, 25 mL of water was added thereto at the same temperature. In the course of cooling the mixture to 5° C., crystals separated out at 14° C. After being stirred at 14° to 24° C. for 1 hour and kept at 2° to 5° C. under ice cooling for 1 hour, the mixture was filtered at the same temperature. The residue was washed with 5 mL of water, to give wet crystals (white). The crystals were dried under reduced pressure at 60° C., to give 4.25 g of crystals (white) of a paroxetine hydrochloride ½ hydrate (yield: 88.3% by weight). The XRD agreed with that of a reference material. The water content was 2.50% by weight (theoretical water content: 2.40% by weight). Its pH of the filtrate was 1.49.

EXAMPLE 4

To a mixed solution of 15.00 g of 2-propanol, 5.74 g of water and 14.24 g (136.70 mmol) of 35% hydrochloric acid was added 5.00 g (13.67 mmol) of a 2-propanol solvate of paroxetine hydrochloride anhydrate (containing about 3% by weight of 2-propanol) under nitrogen gas stream. Although the mixture was heated to 58° C., the solvate was not dissolved. Next, 25 mL of water was added thereto at the same temperature, and the mixture was cooled to 5° C. After being kept at 3° to 5° C. under ice cooling for 1 hour, the mixture was filtered at the same temperature, and the residue was washed with 5 mL of water, to give wet crystals (white). The crystals were dried under reduced pressure at 60° C., to give 4.62 g of crystals (white) of a paroxetine hydrochloride ½ hydrate (yield: 90.2% by weight). The XRD agreed with that of a reference material. Its water content was 2.48% by weight (theoretical water content: 2.40% by weight). The pH of the filtrate was measured. As a result, the pH was 0.0.

EXAMPLE 5

To a mixed solution of 15.00 g of 2-propanol, 14.07 g of water and 1.42 g of 35% hydrochloric acid (equivalent to 13.67 mmol of hydrogen chloride) was added 5.00 g (13.67 mmol) of a 2-propanol solvate of a paroxetine hydrochloride anhydrate (containing about 3% by weight of 2-propanol) under nitrogen gas stream, and the mixture was heated to 40° C. to dissolve the solvate. Next, 25 mL of water was added thereto at the same temperature, and the mixture was cooled to 5° C. After being kept at 2° to 5° C. under ice cooling for 1 hour, the mixture was filtered at the same temperature, and the residue was washed with 5 mL of water, to give wet crystals (white). The crystals were dried under reduced pressure at 60° C., to give 4.67 g of crystals (white) of a paroxetine hydrochloride ½ hydrate (yield: 91.2% by weight). The XRD agreed with that of a reference material. The water content was 2.50% by weight (theoretical water content: 2.40% by weight).

EXAMPLE 6

To a mixed solution of 10.00 g of 2-propanol, 9.07 g of water and 1.42 g (equivalent to 13.67 mmol of hydrogen chloride) of 35% hydrochloric acid was added 5.00 g (13.67 mmol) of a 2-propanol solvate of a paroxetine hydrochloride anhydrate (containing about 3% by weight of 2-propanol) under nitrogen stream, and the mixture was heated to 50° C. Next, 30 mL of water was added thereto at the same temperature. In the course of cooling the mixture to 5° C., crystals separated out at 38° C. After being stirred at 38° to 40° C. for 30 minutes and kept at 3° to 5° C. under ice cooling for 1 hour, the mixture was filtered at the same temperature. The residue was washed with 5 mL of water, to give wet crystals (white). The crystals were dried under reduced pressure at 60° C., to give 4.80 g of crystals (white) of a paroxetine hydrochloride ½ hydrate (yield: 93.8% by weight). The XRD agreed with that of a reference material. The water content was 2.50% by weight (theoretical water content: 2.40% by weight).

EXAMPLE 7

To a mixed solution of 10.00 g of 2-propanol, 9.91 g of water and 0.14 g of 35% hydrochloric acid (equivalent to 1.367 mmol of hydrogen chloride) was added 5.00 g (13.67 mmol) of a 2-propanol solvate of a paroxetine hydrochloride anhydrate (containing about 3% by weight of 2-propanol) under nitrogen gas stream, and the mixture was heated to 50° C. Next, 30 mL of water was added thereto at the same temperature. In the course of cooling the mixture to 5° C., crystals separated out at 33° C. After being stirred at 32° to 33° C. for 30 minutes and kept at 2° to 5° C. under ice cooling for 30 minutes, the mixture was filtered at the same temperature, and the residue was washed with 5 mL of water, to give wet crystals (white). The crystals were dried under reduced pressure at 60° C., to give 4.82 g of crystals (white) of a paroxetine hydrochloride ½ hydrate (yield: 94.1% by weight). The XRD agreed with that of a reference material. The water content was 2.57% by weight (theoretical water content: 2.40% by weight).

EXAMPLE 8

To 38.11 g of a toluene solution containing 7.04 g (16.39 mmol) of crude (−)-(3S,4R)-1-tert-butoxycarbonyl-4-(4-fluorophenyl)-3-[3,4-methylene-dioxyphenyl)oxymethyl] piperidine was added 4.27 g of 35% hydrochloric acid (equivalent to 41.01 mmol of hydrogen chloride) under nitrogen gas stream, and deprotection reaction of tert-butoxycarbonyl group was carried out at 68° to 70° C. for 2 hours. The completion of the reaction was confirmed with HPLC. Next, 40 mL of water was added thereto, to form phase separation (three layers) at 70° C. The upper layer (toluene layer) was removed from the mixture, and the intermediate layer (aqueous layer) and the lower layer (oil layer) were collected. To the intermediate layer and the lower layer, 10.0 g of 2-propanol was added to form a single layer. In addition, 0.33 g of activated carbon was added thereto and the mixture was stirred at 62° to 67° C. for 15 minutes, and thereafter the activated carbon was filtered off. In the course of cooling the resulting solution to 5° C., crystals separated out at 28° C. After being stirred at 38° to 40° C. for 30 minutes and kept at 2° to 5° C. under ice cooling for 30 minutes, the suspension was filtrated at the same temperature. The residue was washed with a solution composed of 1.0 g of 2-propanol and 4.0 g of water, to give wet crystals. The crystals were dried under reduced pressure at 60° C., to give 5.10 g of crystals of a paroxetine hydrochloride ½-hydrate (yield: 85.0% by weight). The XRD agreed with that of a reference material. The water content was 2.70% by weight (theoretical water content: 2.40% by weight).

EXAMPLE 9

Under nitrogen gas stream, 311.91 g of a 2-propanol solution containing 42.95 g (100 mmol) of crude (−)-(3S, 4R)-1-tert-butoxycarbonyl-4-(4-fluorophenyl)-3-[3,4-methylenedioxyphenyl)oxymethyl]piperidine was heated to 65° C., and 26.55 g of a 2-propanol solution of 20.6% hydrogen chloride (equivalent to 150 mmol of hydrogen chloride) was added dropwise thereto. The deprotection reaction of tert-butoxycarbonyl group was carried out at 68° to 73° C. for 2 hours. The completion of the reaction was confirmed with HPLC. Next, 93 mL of 2-propanol containing isobutene was distilled off under normal pressure. During this procedure, 93.5 mL of 2-propanol was added dropwise thereto to maintain the amount of the liquid. Further, 2.41 g of activated carbon was added thereto, the mixture was stirred at 80° to 82° C. for 15 minutes, and thereafter the activated carbon was filtered off. The filter cake was washed with 43 mL of 2-propanol. After refluxing the filtrate for 15 minutes, in the course of cooling the solution to 5° C., crystals separated out at 55° C. After being kept at 5° C. under ice cooling for 1 hour, the suspension was filtrated at the same temperature. The residue was washed with 94.5 mL of 2-propanol, to give 59.80 g (calculated yield after drying: 86.5% by weight) of wet crystals of a 2-propanol solvate of a paroxetine hydrochloride anhydrate (saturated with 2-propanol; containing about 14% by weight of 2-propanol). The crystals were divided into some portions to carry out the following experiments 1) to 3).

1) To a mixed solution of 8.04 g of 2-propanol, 15.18 g of water and 0.22 g (equivalent to 2.09 mmol of hydrogen chloride) of 35% hydrochloric acid was added 14.94 g (corresponding to 20.96 mmol of dry product) of the wet crystals of a 2-propanol solvate of a paroxetine hydrochloride anhydrate under nitrogen stream, and the mixture was heated to 50° C. Next, 45.96 g of water was added thereto at the same temperature. In the course of cooling the mixture to 5° C., crystals separated out at 31° C. After being stirred at 31° to 34° C. for 30 minutes and kept at 2° to 5° C. under ice cooling for 30 minutes, the mixture was filtered at the same temperature. The residue was washed with 7.7 mL of water, to give wet crystals (white). The crystals were dried under reduced pressure at 60° C., to give 7.42 g of crystals (white) of a paroxetine hydrochloride ½ hydrate (yield: 94.5% by weight). The XRD agreed with that of a reference material. The water content was 2.57% by weight (theoretical water content: 2.40% by weight). The pH of the supernatant of a suspension prepared by suspending 1 g of the crystals in 10 g of distilled water was 5.21.

2) Wet crystals of a 2-propanol solvate of a paroxetine hydrochloride anhydrate in an amount of 16.10 g were dried under reduced pressure at 25° C., to give 9.55 g of a 2-propanol solvate of a paroxetine hydrochloride anhydrate containing 14.4% by weight of 2-propanol.

Next, 7.16 g (16.76 mmol) of this 2-propanol solvate of a paroxetine hydrochloride anhydrate was added to a mixed solution of 11.23 g of 2-propanol, 12.15 g of water and 0.17 g of 35% hydrochloric acid (equivalent to 1.68 mmol of hydrogen chloride) under nitrogen gas stream, and the mixture was heated to 50° C. Subsequently, 49.05 g of water was added thereto at the same temperature. In the course of cooling the mixture to 5° C., crystals separated out at 33° C. After being stirred at 33° to 38° C. for 30 minutes and kept at 2° to 5° C. for 30 minutes, the mixture was filtered at the same temperature. The residue was washed with 8.2 mL of water, to give wet crystals (white). The crystals were dried under reduced pressure at 60° C., to give 6.00 g of crystals (white) of a paroxetine hydrochloride ½ hydrate (yield: 95.5% by weight). The XRD agreed with that of a reference material. The water content was 2.60% by weight (theoretical water content: 2.40% by weight). The pH of the supernatant of a suspension prepared by suspending 1 g of the crystals in 10 g of distilled water was 5.51.

3) The above-mentioned wet crystals of a 2-propanol solvate of a paroxetine hydrochloride anhydrate in an amount of 13.05 g were dried under reduced pressure at 80° C., to give 6.90 g of a 2-propanol solvate of a paroxetine hydrochloride anhydrate containing 3.0% by weight of 2-propanol.

Next, 5.00 g (13.26 mmol) of this 2-propanol solvate of a paroxetine hydrochloride anhydrate was added to a mixed solution of 9.55 g of 2-propanol, 9.61 g of water and 0.14 g (equivalent to 1.33 mmol of hydrogen chloride) of 35% hydrochloric acid under nitrogen gas stream, and the mixture was heated to 50° C. Subsequently, 29.10 g of water was added thereto at the same temperature. In the course of cooling the mixture to 5° C., crystals separated out at 30° C. After being stirred at 30° to 35° C. for 30 minutes and kept at 10 to 5° C. under ice cooling for 30 minutes, the mixture was filtered at the same temperature. The residue was washed with 4.9 mL of water, to give wet crystals. The crystals were dried under reduced pressure at 60° C., to give 4.71 g of crystals (white) of a paroxetine hydrochloride ½ hydrate (yield: 94.8% by weight). The XRD agreed with that of a reference material. The water content was 2.60% by weight (theoretical water content: 2.40% by weight). The pH of the supernatant of a suspension prepared by suspending 1 g of the crystals in 10 g of distilled water was 4.98.

EXAMPLE 10

Under nitrogen gas stream, 5.00 g (13.34 mmol) of crystals of a paroxetine hydrochloride ½ hydrate which had been once colored in pink were added to a mixed solution of 10.00 g of 2-propanol, 9.07 g of water and 1.39 g (equivalent to 13.34 mmol of hydrogen chloride) of 35% hydrochloric acid, and the mixture was heated to 50° C. Next, 30 mL of water was added thereto at the same temperature. In the course of cooling the mixture to 5° C., crystals separated out at 36° C. After being stirred at 36° to 39° C. for 30 minutes and kept at 1° to 5° C. under ice cooling for 1 hour, the mixture was filtered at the same temperature. The residue was washed with 5 mL of water, to give wet crystals (white). The crystals were dried under reduced pressure at 60° C., to give 4.91 g of crystals (white) of a paroxetine hydrochloride ½ hydrate (yield: 98.2% by weight). The XRD agreed with that of a reference material. The water content was 2.55% by weight (theoretical water content: 2.40% by weight).

EXAMPLE 11

Under nitrogen gas stream, 7.50 g (20.01 mmol) of crystals of a paroxetine hydrochloride ½ hydrate being colored in pink were added to a mixed solution of 15.0 g of 2-propanol, 9.09 g of water and 2.08 g (equivalent to 20.01 mmol of hydrogen chloride) of 35% hydrochloric acid, and the mixture was heated to 50° C. Next, 45 mL of water was added thereto at the same temperature. In the course of cooling the mixture to 5° C., crystals separated out at 37° C. After being stirred at 37° to 40° C. for 30 minutes and kept at 2° to 5° C. under ice cooling for 30 minutes, the mixture was filtered at the same temperature. The residue was washed with 7.5 g of water, to give wet crystals. The crystals were dried under reduced pressure at 60° C., to give 7.33 g of crystals (yellowish white) of a paroxetine hydrochloride ½ hydrate (yield: 97.7% by weight).

In the above-mentioned example, when 35% hydrochloric acid was not added, the crystals of a paroxetine hydrochloride ½ hydrate were colored in pink.

EXAMPLE 12

To a mixed solution of 5.0 g of 2-propanol, 4.91 g of water and 0.14 g (equivalent to 1.367 mmol of hydrogen chloride) of 35% hydrochloric acid was added 5.00 g (13.67 mmol) of a 2-propanol solvate of a paroxetine hydrochloride anhydrate (containing about 3% by weight of 2-propanol) under nitrogen gas stream, and the mixture was heated to 52° C. Next, 40 mL of water was added thereto at 48° to 49° C. In the course of cooling the mixture to 5° C., crystals separated out at 43° C. After being stirred at 43° to 45° C. for 30 minutes and kept at 2° to 5° C. under ice cooling for 30 minutes, the mixture was filtered at the same temperature. The residue was washed with 5 mL of water, to give wet crystals (white). The crystals were dried under reduced pressure at 60° C., to give 4.80 g of crystals (white) of a paroxetine hydrochloride ½ hydrate (yield: 93.7% by weight).

EXAMPLE 13

To a mixed solution of 7.05 g of 2-propanol, 7.41 g of water and 0.14 g of 35% hydrochloric acid (equivalent to 1.367 mmol of hydrogen chloride) was added 5.00 g (13.67 mmol) of a 2-propanol solvate of a paroxetine hydrochloride anhydrate (containing about 3% by weight of 2-propanol)

under nitrogen gas stream, and the mixture was heated to 45° C. Next, 35 mL of water was added thereto at 45° to 50° C. In the course of cooling the mixture to 5° C., crystals separated out at 36° C. After being stirred at 36° to 38° C. for 30 minutes and kept at 2° to 5° C. under ice cooling for 30 minutes, the mixture was filtered at the same temperature. The residue was washed with 5 mL of water, to give wet crystals (white). The crystals were dried under reduced pressure at 60° C., to give 4.78 g of crystals (white) of a paroxetine hydrochloride ½ hydrate (yield: 93.3% by weight).

EXAMPLE 14

To a solution of 37.5 g of water and 0.11 g of 35% hydrochloric acid was added 3.75 g (10.25 mmol) of a 2-propanol solvate of a paroxetine hydrochloride anhydrate under nitrogen gas stream, and the mixture was heated to 75° C. After the solvate was dissolved, the mixture was cooled. As a result, crystals separated out at 53° C., and the mixture was solidified at 50° C. Subsequently, 18.8 g of water was added thereto, to suspend the crystals. The suspension was then cooled and filtrated at 24° C. The residue was washed with 3.75 g of water, to give wet crystals. The crystals were dried under reduced pressure at 60° C., to give 3.34 g of crystals (white) of a paroxetine hydrochloride ½ hydrate (yield: 87.0% by weight). The XRD agreed with that of a reference material. The water content was 2.36% by weight (theoretical water content: 2.40% by weight). The pH of the supernatant of a suspension prepared by suspending 1 g of the crystals in 10 g of distilled water was 5.41.

On the other hand, the crystals obtained in the same manner as in recrystallization in water in the absence of hydrochloric acid disclosed in JP-B-6-47587 and item (b) of Example 3 of European Patent No. 223403 showed pink color under both of wet conditions and dry conditions. The pH of the supernatant of a suspension prepared by suspending 1 g of the crystals in 10 g of distilled water was 6.30.

EXAMPLE 15

To a mixed solution of 7.5 g of 2-propanol, 7.4 g of water and 0.14 g (equivalent to 1.367 mmol of hydrogen chloride) of 35% hydrochloric acid was added 5.00 g (13.67 mmol) of a 2-propanol solvate of a paroxetine hydrochloride anhydrate (containing about 3% by weight of 2-proapnol) under nitrogen gas stream, and the mixture was heated under reflux (82° C.) for 1 hour, to dissolve the solvate. Next, when the temperature attained to about 50° C., 25 mL of water was added thereto, and the mixture was cooled to 5° C. After being kept at 2 to 5° C. for 1 hour, the mixture was filtered at the same temperature. The residue was washed with 5 mL of water, to give wet crystals (white). The crystals were dried under reduced pressure at 60° C., to give crystals (white) of a paroxetine hydrochloride ½ hydrate. The pH of the supernatant of a suspension prepared by suspending 1 g of the crystals in 10 g of distilled water was 4.96.

On the other hand, the crystals of a paroxetine hydrochloride ½ hydrate were prepared in the same manner as mentioned above except that 35% hydrochloric acid was not added. The crystals showed pink color under both of wet conditions and dry conditions. The pH of the supernatant of a suspension prepared by suspending 1 g of the crystals in 10 g of distilled water was 6.99.

From these results, it can be seen that crystals of a paroxetine hydrochloride ½ hydrate efficiently separate out in a solvent for crystallization according to Invention 1, and that white crystals of a paroxetine hydrochloride ½ hydrate which are not colored in pink efficiently separate out according to Invention 2.

INDUSTRIAL APPLICABILITY

Crystals of a paroxetine chloride ½ hydrate can be utilized as an antidepressant.

The invention claimed is:

1. A method for producing crystals of paroxetine hydrochloride ½-hydrate comprising adding water to a solution or suspension comprising paroxetine hydrochloride and a polar organic solvent which contains at most 60% by weight of water, to adjust the water content of said solution or suspension to at least 70% by weight whereby crystals of paroxetine hydrochloride ½-hydrate are caused to separate out in said water-containing polar organic solvent.

2. The method according to claim 1, wherein a solution or suspension of a solid or oily paroxetine hydrochloride is initially prepared, and water is added to the solution or suspension to adjust the water content to at least 70% by weight.

3. The method according to claim 1, wherein a solution or suspension of crystals of paroxetine hydrochloride is initially prepared, and water is added to the solution or suspension to adjust the water content to at least 70% by weight.

4. The method according to claim 1, wherein a solution or suspension of crystals of paroxetine hydrochloride anhydrate is initially prepared, and water is added to the solution or suspension to adjust the water content to at least 70% by weight.

5. The method according to claim 1, wherein a solution or suspension of crystals of 2-propanol solvate of paroxetine hydrochloride anhydrate obtained by crystallization from 2-propanol is initially prepared, and water is added to the solution or suspension to adjust the water content to at least 70% by weight.

6. The method according to claim 1, wherein a solution or suspension of crystals of paroxetine hydrochloride ½-hydrate is initially prepared, and water is added to the solution or suspension to adjust the water content to at least 70% by weight.

7. The method according to claim 1, wherein water is added to a solution or suspension comprising paroxetine hydrochloride and a polar organic solvent containing 15 to 55% by weight of water.

8. The method according to claim 1, wherein water is added to a solution or suspension comprising paroxetine hydrochloride and a polar organic solvent containing 20 to 50% by weight of water.

9. The method according to claim 1, wherein water is added to the solution or suspension comprising paroxetine hydrochloride at a temperature of 40° to 60° C.

10. The method according to claim 1, wherein water is added to the solution or suspension of paroxetine hydrochloride, and then the resulting solution or suspension is cooled to a temperature of 0° to 10° C.

11. The method according to claim 1, wherein the polar organic solvent is a lower alcohol having 1 to 5 carbon atoms or a ketone.

12. The method according to claim 11, wherein the lower alcohol is 2-propanol.

13. The method according to claim 1, wherein hydrogen chloride is present in the solution or suspension of paroxetine hydrochloride.

14. A method for producing crystals of paroxetine hydrochloride ½-hydrate wherein crystals of paroxetine hydrochloride ½-hydrate are allowed to separate out from a solution or suspension of paroxetine hydrochloride in which water or a water-containing polar organic solvent is used as a solvent in the presence of hydrogen chloride, with the proviso that concentrated hydrochloric acid is not added to an aqueous solution of paroxetine acetate.

15. The method according to claim 14, wherein the pH of the solution or suspension of paroxetine hydrochloride is at most 2.

16. The method according to claim 14, wherein a solution or suspension of a solid or oily paroxetine hydrochloride is initially prepared, and water is added to the solution or suspension to adjust the water content to at least 70% by weight.

17. The method according to claim 14, wherein a solution or suspension of crystals of paroxetine hydrochloride is initially prepared, and water is added to the solution or suspension to adjust the water content to at least 70% by weight.

18. The method according to claim 14, wherein a solution or suspension of crystals of paroxetine hydrochloride anhydrate is initially prepared, and water is added to the solution or suspension to adjust the water content to at least 70% by weight.

19. The method according to claim 18, wherein the crystals of paroxetine hydrochloride anhydrate are crystals of 2-propanol solvate of paroxetine hydrochloride anhydrate obtained by crystallization in 2-propanol.

20. The method according to claim 14, wherein a solution or suspension of crystals of paroxetine hydrochloride ½-hydrate is initially prepared, and water is added to the solution or suspension to adjust the water content to at least 70% by weight.

21. A process for preparing crystals of paroxetine hydrochloride ½-hydrate being not colored in pink, comprising dissolving crystals of paroxetine hydrochloride ½-hydrate being colored in pink in a solvent, and allowing the crystals to separate out wherein the crystals are recovered from said solvent in the presence of hydrogen chloride in an amount at least equimolar with the paroxetine hydrochloride ½-hydrate.

\* \* \* \* \*